(12) United States Patent
Huang et al.

(10) Patent No.: US 11,273,446 B2
(45) Date of Patent: Mar. 15, 2022

(54) FLUIDIC FITTINGS COMPRISING ELECTRO-FLUIDIC LEAK DETECTION ELEMENTS AND FLUID HANDLING SYSTEMS INCORPORATING THE SAME

(71) Applicant: Bio-Chem Fluidics, Inc., Boonton, NJ (US)

(72) Inventors: Henry X Huang, Edison, NJ (US); Ethan Matthew Gardner, Hoboken, NJ (US); Razvan Bulugioiu, Mountain Lakes, NJ (US); Michael Swern, Boonton, NJ (US); William A Easterbrook, Clinton, NJ (US); Sharad Harihar Joshi, Sr., Morristown, NJ (US)

(73) Assignee: BIO-CHEM FLUIDICS, INC., Boonton, NJ (US)

( * ) Notice: Subject to any disclaimer, the term of this patent is extended or adjusted under 35 U.S.C. 154(b) by 271 days.

(21) Appl. No.: 16/527,542

(22) Filed: Jul. 31, 2019

(65) Prior Publication Data
US 2020/0038865 A1 Feb. 6, 2020

Related U.S. Application Data

(60) Provisional application No. 62/712,752, filed on Jul. 31, 2018.

(51) Int. Cl.
*B01L 3/00* (2006.01)

(52) U.S. Cl.
CPC ... *B01L 3/502746* (2013.01); *B01L 3/502715* (2013.01); *B01L 2200/0689* (2013.01); *B01L 2300/0645* (2013.01); *B01L 2400/082* (2013.01)

(58) Field of Classification Search
CPC ...... A61M 2039/1022; A61M 2205/15; A61M 39/10; A61M 39/12; A61M 5/16831;
(Continued)

(56) References Cited

U.S. PATENT DOCUMENTS 5,090,871 A 2/1992 Story et al.
5,402,075 A * 3/1995 Lu ........................... G01R 1/07
324/664

(Continued)

FOREIGN PATENT DOCUMENTS

EP 1760444 A2 3/2007
WO 2019120453 A1 6/2019

OTHER PUBLICATIONS

International Search Report and Written Opinion dated Oct. 9, 2019 pertaining to International Application No. PCT/US2019/044124 filed Jul. 30, 2019, 14 pgs.

(Continued)

*Primary Examiner* — Jennifer Wecker
*Assistant Examiner* — Jonathan Bortoli
(74) *Attorney, Agent, or Firm* — Dinsmore & Shohl, LLP

(57) ABSTRACT

A threaded fluidic fitting may include a fluid passage, at least one fluid port, a threaded fitting portion, an engageable body portion, and an electro-fluidic leak detection element. The fluid passage extends from the fluid port of the threaded fluidic fitting. The threaded fitting portion comprises a helical thread, extends from a leak detection face of the engageable body portion, and is configured to rotate with the engageable body portion to enhance a fluidically sealed engagement of one of the fluid ports with a complementary fluidic component. The electro-fluidic leak detection element is positioned on the leak detection face of the engageable body portion or on a drip edge portion of a face extending from the leak detection face. A fluid handling
(Continued)

system may include a plurality of threaded fluidic fittings and a leak detecting computing hub in communication with the plurality of threaded fluidic fittings.

22 Claims, 2 Drawing Sheets

(58) Field of Classification Search
CPC ..... B01L 2200/0689; B01L 2300/0645; B01L 2400/082; B01L 3/502715; B01L 3/502746
See application file for complete search history.

(56) References Cited

U.S. PATENT DOCUMENTS

| | | | |
|---|---|---|---|
| 5,744,701 A | 4/1998 | Peterson et al. | |
| 6,144,209 A | 11/2000 | Raymond et al. | |
| 7,316,154 B1* | 1/2008 | Bennett | F16J 15/064 |
| | | | 277/320 |
| 2010/0244438 A1* | 9/2010 | Johanson | F16L 33/30 |
| | | | 285/148.21 |
| 2011/0154886 A1 | 6/2011 | Carns et al. | |
| 2011/0199220 A1 | 8/2011 | McAlister | |
| 2012/0167669 A1 | 7/2012 | Raghavendra et al. | |
| 2012/0255343 A1 | 10/2012 | Sarma et al. | |
| 2012/0272722 A1 | 11/2012 | Khalifa et al. | |
| 2013/0180318 A1* | 7/2013 | Howard | G01M 3/04 |
| | | | 73/49.2 |

OTHER PUBLICATIONS

Baar et al. "Micromachined Two Dimensional Resistor Arrays for Determination of Gas Parameiers" MESA+ Research Insitute, University of Twente, Jun. 2003,4 pgs.

Bryant "monitoring meets the IoT" https://www.cloud28plus.com/emea/content/Predictive-maintenance-machine-condition-monitoring-meets-the-IoT, 8 pgs.

RLE Technologies "Leak Detection Sensing Cable" www.rietech.com, 2 pgs.

Sadeghioon et al. "SmartPipes: Smart Wireless Sensor Networks for Leak Detection in Water Pipelines" Journal of Sensor and Actuator Networks, J. Sens. Actuator Netw. 2014, 3, 64-78, 15 pgs.

* cited by examiner

FLUIDIC FITTINGS COMPRISING ELECTRO-FLUIDIC LEAK DETECTION ELEMENTS AND FLUID HANDLING SYSTEMS INCORPORATING THE SAME

CROSS-REFERENCE TO RELATED APPLICATIONS

This application claims the benefit of U.S. Provisional Application Ser. No. 62/712,752 (BCF 0009 MA), filed Jul. 31, 2018.

BACKGROUND

The present disclosure relates to fluidic fittings and, more particularly, to leak detection or failure prediction in fluidic fittings and fluid handling systems incorporating the same.

BRIEF SUMMARY

Microfluidic systems typically require fluidic coupling of similar or dissimilar fluidic components, like silicone or other polymeric tubing, or pumps, valves, manifolds, reservoirs, micro-fluidic chips, or other fluidic instruments or accessories. These fluidic components can be placed in fluid communication with each other using fluidic fittings, which come in a variety of configurations. For example, a fluidic fitting may be configured as a tube-to-tube fitting, including straight tube connectors, Y (wye) connectors, multiport connectors, elbow fittings, tee fittings, with or without reducers, and with any of a variety of barb styles. A fluidic fitting may also be configured as a Luer fitting, a partially or fully threaded fitting, a quick connect coupling, a fluidic union or adapter, etc. Regardless of the particular fitting design, for the purposes of defining and describing the subject matter of the present disclosure, it is noted that a fluidic fitting should be understood to encompass any fluidic component that creates a sealed and secure fluidic coupling between two fluidic components.

According to the subject matter of the present disclosure, fluidic fittings are provided with an electro-fluidic leak detection element as a means to monitor the performance of the fitting. As is described in further detail below, the electro-fluidic leak detection element may comprise multiple components including, for example, a printed circuit substrate with flexible and/or rigid portions, one or more fluid sensing portions secured to the printed circuit substrate, and associated printed circuitry.

In accordance with one embodiment of the present disclosure, a threaded fluidic fitting comprises a fluid passage, at least one fluid port, a threaded fitting portion, an engageable body portion, and an electro-fluidic leak detection element. The fluid passage extends from the fluid port of the threaded fluidic fitting. The threaded fitting portion comprises a helical thread, extends from a leak detection face of the engageable body portion, and is configured to rotate with the engageable body portion to enhance a fluidically sealed engagement of one of the fluid ports with a complementary fluidic component. The electro-fluidic leak detection element is positioned on the leak detection face of the engageable body portion or on a drip edge portion of a face extending from the leak detection face of the engageable body portion In accordance with another embodiment of the present disclosure, a barbed fluidic fitting comprises a fluid passage, at least one fluid port, a barbed fitting portion, and an electro-fluidic leak detection element. The fluid passage extends from the fluid port of the barbed fluidic fitting. The barbed fitting portion comprises a barb shank and a sealing barb. The sealing barb and the barb shank are configured to form a sealed engagement with an inside diameter of an end portion of a length of fluidic tubing. The electro-fluidic leak detection element is positioned on the barb shank.

In accordance with another embodiment of the present disclosure, a fluid handling system comprises a plurality of threaded fluidic fittings, according to one or more embodiments described herein, and a leak detecting computing hub in communication with the plurality of threaded fluidic fittings. The leak detecting computing hub is configured to identify individual fittings of the plurality of fittings and process fluid leakage signals from each of the identified fittings. The leak detecting computing hub is further configured to build and store diagnostic data for each of the threaded fluidic fittings from the processed fluid leakage signals.

In accordance with another embodiment of the present disclosure, a fluid handling system comprises a plurality of barbed fluidic fittings, according to one or more embodiments described herein, and a leak detecting computing hub in communication with the plurality of barbed fluidic fittings. The leak detecting computing hub is configured to identify individual fittings of the plurality of fittings and process fluid leakage signals from each of the identified fittings. The leak detecting computing hub is further configured to build and store diagnostic data for each of the threaded fluidic fittings from the processed fluid leakage signals.

Although the concepts of the present disclosure are described herein with primary reference to one particular type of fluidic fitting, i.e., a fitting comprising a threaded fitting portion and a barbed fitting portion, it is contemplated that the concepts will enjoy applicability to any type of fluidic fitting.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
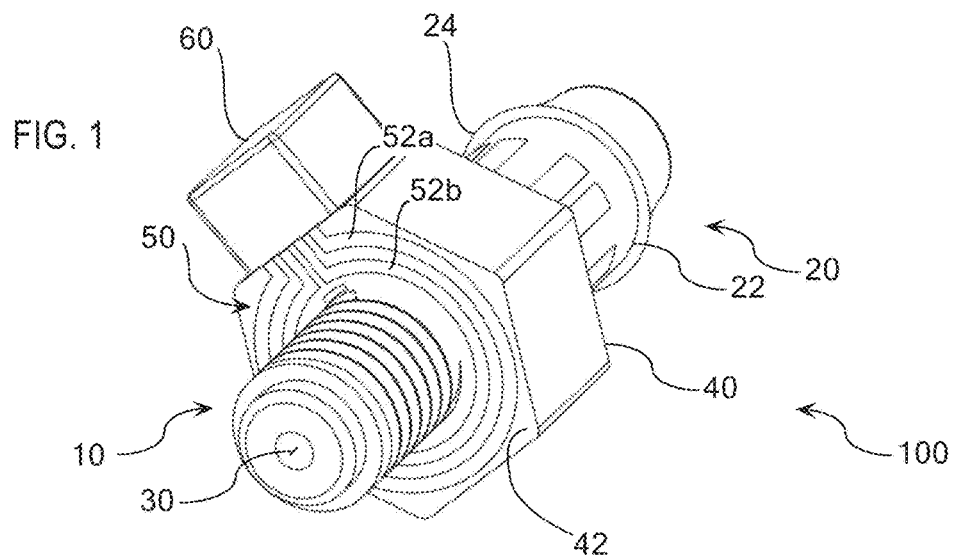
FIG. 1 illustrates a fluidic fitting according to one embodiment of the present disclosure, with particular emphasis on the threaded fitting portion and the leak detection face of an engageable body portion of the fitting.
Figure 2:
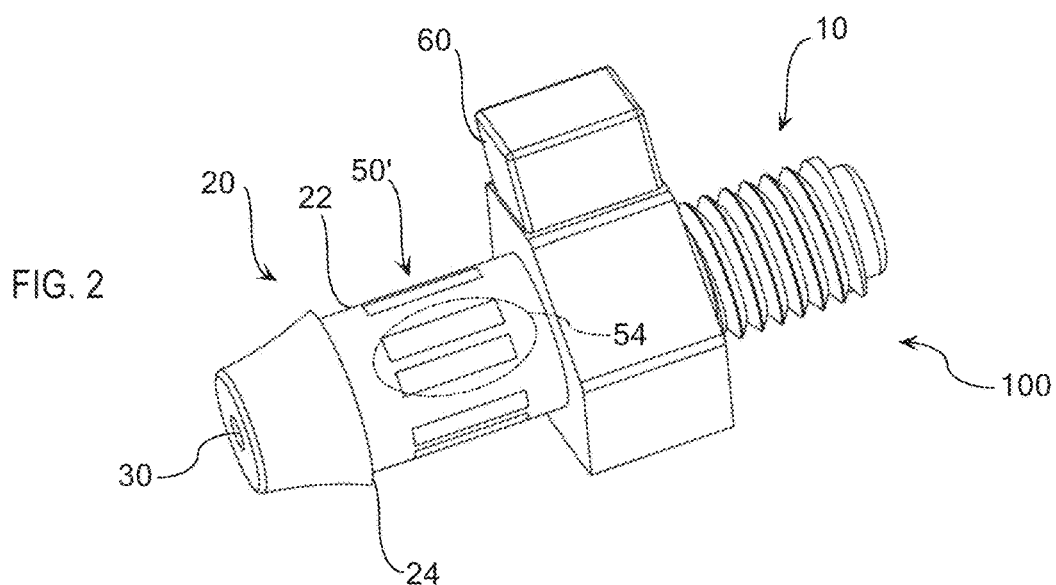
FIG. 2 illustrates a fluidic fitting according to another embodiment of the present disclosure, with particular emphasis on the barbed fitting portion of the fitting.

Referring initially to FIGS. 1 and 2, a fluidic fitting 100 is illustrated comprising a threaded fitting portion 10 and a barbed fitting portion 20. The fluidic fitting 100 comprises a fluid passage extending longitudinally between two fluid ports 30 at opposite ends of the fitting 100. For the purposes of the present disclosure, if a particular fitting comprises a threaded fitting portion 10 it can be described as a "threaded" fluidic fitting, regardless of whether the fitting also comprises a barbed fitting portion 20 or some other type of fitting portion. Similarly, if a particular fitting comprises a barbed fitting portion 20, it can be described as a "barbed" fluidic fitting regardless of whether the fitting also comprises a threaded fitting portion 10 or some other type of fitting portion. Accordingly, for example, the fitting illustrated in FIGS. 1 and 2 is referenced herein as either a "threaded" fluidic fitting, a "barbed" fluidic fitting, or both, depending on context.

Referring specifically to FIG. 1, the fluidic fitting 100 comprises an engageable body portion 40 and an electro-fluidic leak detection element 50. The threaded fitting portion 10 comprises a helical thread 12, extends from a leak detection face 42 of the engageable body portion 40, and is configured to rotate with the engageable body portion 40. The engageable motion of the threaded fitting portion 10 allows it to advance into sealed engagement with a complementary fluidic component carrying a complementary threaded portion to enhance a fluidically sealed engagement of one of the fluid ports 30 with the complementary fluidic component. The complementary fluidic component may be any of a variety of similar or dissimilar fluidic components including, for example, a pump, valve, fluid manifold, fluid reservoir, micro-fluidic chip, or any other fluidic instrument or accessory, the particular nature of which is beyond the scope of the present disclosure. In some embodiments, fluidic fittings contemplated herein may comprise only one fluid port, as would be the case with, for example, a pressure relief fitting, or more than two fluid portions, as would be the case with, for example, a multi-directional fluidic fitting.

As is illustrated in FIG. 1, the electro-fluidic leak detection element 50 is positioned on the leak detection face 42 of the engageable body portion 40 to provide an indication of the condition of the aforementioned fluidically sealed engagement. More specifically, the electro-fluidic leak detection element 50 may be configured as a sensing portion that surrounds a majority of a perimeter of the threaded fitting portion 10, where the threaded fitting portion 10 extends from the leak detection face 42 of the engageable body portion 40. In more particular embodiments, the electro-fluidic leak detection element 50 can be configured as a pair of concentric spaced electrodes 52a, 52b surrounding a majority of the threaded fitting portion 10 where the threaded fitting portion 10 extends from the leak detection face 42. In some embodiments, the electro-fluidic leak detection element 50 may surround less than a majority of the threaded fitting portion 10 and still provide for sufficient leak detection.

Figure 3:
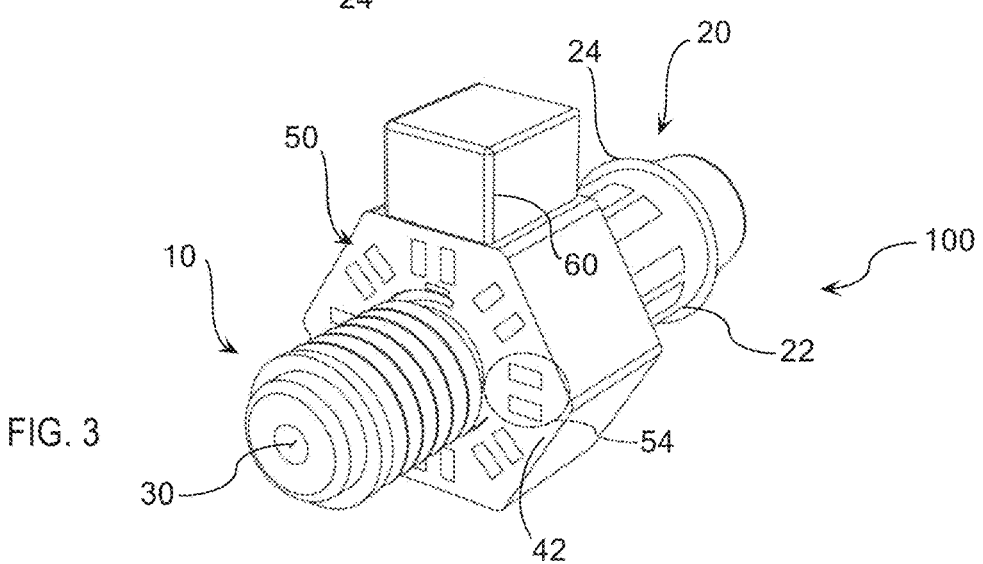
FIG. 3 illustrates a fluidic fitting according to another embodiment of the present disclosure, with particular emphasis on the threaded fitting portion and the leak detection face of an engageable body portion of the fitting.

Alternatively, referring to the embodiment illustrated in FIG. 3, the electro-fluidic leak detection element 50 can be configured as a plurality of spaced paired electrodes 54, or other types of spaced sensing portions, surrounding a majority of a perimeter of the threaded fitting portion 10 where the threaded fitting portion 10 extends from the leak detection face 42 of the engageable body portion 40. Regardless of whether the spaced sensing portions comprise paired electrodes 54, paired sensing pads, or other types of paired or unpaired sensing portions, it is contemplated that they may be arranged along a common circumference to increase the precision or uniformity at which leaks are detected. It is also contemplated that sensing portions may alternatively or additionally be provided on a drip edge portion of a face extending from the leak detection face 42 of the engageable body portion. In the embodiment illustrated in FIG. 3, any of the six flat nut faces extending orthogonally from the leak detection face 42 may comprise a drip edge portion where additional or alternative sensing portions may be positioned to detect leaking fluid as it runs down the leak detection face 42 and drips along the drip edge portion on the orthogonal nut faces of the engageable body portion 40.

Referring further to FIGS. 1 and 3, it is noted that the electro-fluidic leak detection element 50 may be positioned completely outside of the threaded fitting portion 10 on the leak detection face 42 of the engageable body portion 40. It is further contemplated that the leak detection face 42 of the engageable body portion may be planar and that the threaded fitting portion 10 may comprise a helical thread 12 comprising an axis of rotation that intersects a plane of the leak detection face 42. More specifically, the axis of rotation of the helical thread 12 may be orthogonal to a plane of the leak detection face 42.

The barbed fitting portion 20 and additional electro-fluidic leak detection element 50' of the fluidic fitting 100 are illustrated most completely in FIG. 2. The barbed fitting portion 20 comprises a barb shank 22 and a sealing barb 24. The sealing barb 24 and the barb shank 22 are configured to form a sealed engagement with an inside diameter of an end portion of a length of fluidic tubing in a manner which may be conveniently gleaned from the state of the art and will be apparent to those practicing the technology of the present disclosure. As is illustrated in FIG. 2, the additional electro-fluidic leak detection element 50' is positioned on the barb shank 22 so that fluid passing beyond a sealed interface between the sealing barb 24 and the associated tubing, will be detected by the additional electro-fluidic leak detection element 50'.

In FIG. 2, the additional electro-fluidic leak detection element 50' is configured as a plurality of spaced sensing portions, e.g., a plurality of electrodes or other sensing portions 54 that are arranged about an outer circumferential surface of the barb shank 22. Embodiments with a single sensing portion are also contemplated. The sensing portions 54 may be evenly spaced about the shank 22 or may be arranged in pairs by adjusting the spacing between the sensing portions 54 so that some sensing portions 54 are closer to each other than remaining sensing portions 54. As is described in further detail herein with reference to FIG. 4, the additional electro-fluidic leak detection element 50' may comprise a printed circuit substrate, which may be conveniently mounted to the barb shank 22.

Figure 4:
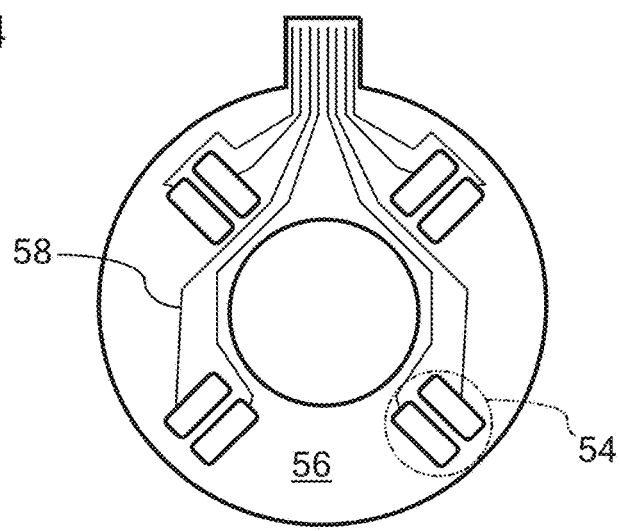
FIG. 4 illustrates components of an electro-fluidic leak detection element according to some embodiments of the present disclosure.

Referring to FIG. 4, the electro-fluidic leak detection element 50, 50' may comprise a rigid or flexible printed circuit substrate 56, fluid sensing portions in the form of a plurality of paired electrodes 54, and printed circuitry 58 electrically coupled to the fluid sensing portions, i.e., the paired electrodes 54. The fluid sensing portions and the associated printed circuitry 58 can be secured to the printed circuit substrate 56, which may be mounted to the leak detection face 42 of the engageable body portion 40 illustrated in FIG. 3. The concentric spaced electrodes 52a, 52b of the embodiment illustrated in FIG. 1 may similarly be formed on a rigid or flexible printed circuit substrate. It is further contemplated that the fluid sensing portions and the associated printed circuitry may be coated with a polymer selected to be resistant to degradation when in contact with fluid.

Referring to FIGS. 1-3, it is noted that the leak detection element 50 may further comprise a leak detection module 60 in communication with the fluid sensing portions of the electro-fluidic leak detection element 50 via, for example, the aforementioned printed circuitry. The leak detection module may be secured to an outer surface of the fluidic fitting 100. In the embodiments of FIGS. 1-3, the leak detection module 60 is secured to the engageable body portion 40 of the fluidic fitting 100. Regardless of the manner in which the leak detection module 60 communicates with the fluid sensing portions of the leak detection element 50, it is contemplated that the leak detection module 60 can be programmed to cooperate with the leak detection element 50 to generate a fluid leakage signal that is indicative of a degree of leakage at the fluidic fitting 100. It is contemplated that the leak detection module 60 and the leak detection element may be part of a single integrated component and that either or both components may be configured to function as a stand-alone embedded analysis monitor.

Depending on the configuration of the fluid sensing portions of the leak detection element 50, the fluid leakage signal may be a single component signal with a magnitude or other signal characteristic that is indicative of a degree of leakage at the threaded fluidic fitting, or a multi-component signal that collectively indicates a degree of leakage at the fluidic fitting 100. It is also contemplated that the fluid leakage signal may be manifested in a variety of ways. For example, the signal may be a digital or analog representation of the degree of leakage, or a more simple visual representation of the degree of leakage in the form of, e.g., a green, red, or yellow indicator, an auditory indicator, etc.

Although the fluid sensing portions of the electro-fluidic leak detection elements 50 are illustrated in FIGS. 1-4 as a plurality of paired electrodes, it is contemplated that these sensing portions may take a variety of forms including, for example, conductive fluid sensors, resistive fluid sensors, capacitive fluid sensors, optical fluid sensors, or combinations thereof.

Further, it is contemplated that although the engageable body portion 40 is illustrated in FIGS. 1-3 as a tool-receiving nut, it is contemplated that the engageable body portion 40 may take a variety of forms including, for example, a manually-engageable, knurled or un-knurled, gripping portion, or any in any of a variety of conventional or yet-to-be developed surface configurations that serve as an effective means for rotating the threaded fitting portion 10 to create a fluidic seal between one of the fluid ports 30 and a complementary fluidic component.

Figure 5:
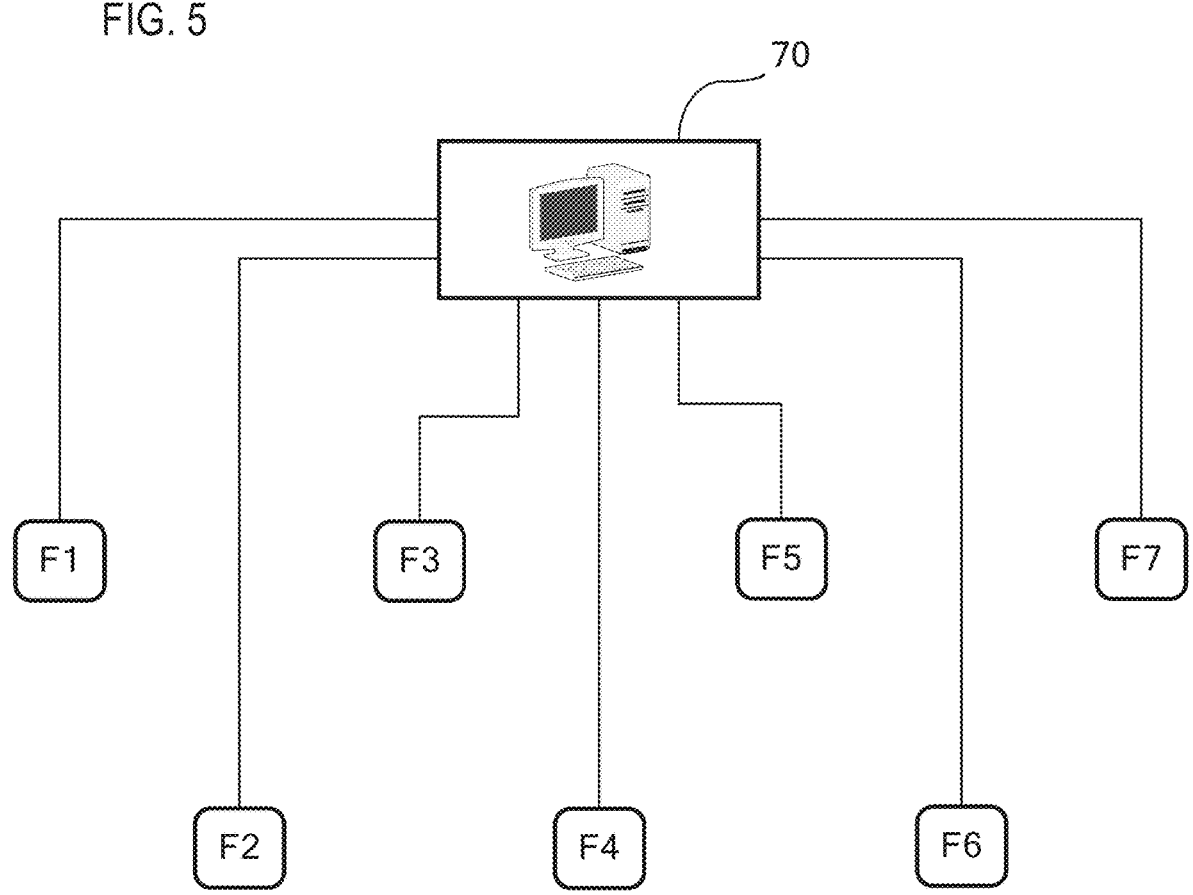
FIG. 5 is a schematic illustration of a fluid handling system according to one embodiment of the present disclosure, and it should be understood that suitable configurations may take a variety of forms depending on the particular application of the technology disclosed herein.

Referring finally to FIG. 5, the present disclosure also encompasses a fluid handling system comprising a plurality of fluidic fittings F1, F2, F3, etc., and a leak detecting computing hub 70 in communication with the plurality of fluidic fittings F1, F2, F3, etc. The leak detecting computing hub 70 comprises suitable embedded processor(s), logic module(s), and other supporting circuitry that are collectively configured to identify individual fittings of the plurality of fittings F1, F2, F3, etc., and process fluid leakage signals from each of the identified fittings F1, F2, F3, etc. In this manner, the leak detecting computing hub 70 can be configured to build and store diagnostic data for each of the fluidic fittings F1, F2, F3, etc., from the processed fluid leakage signals. It is noted that the leak detecting computing hub 70 may communicate with the fittings F1, F2, F3, etc., in any conventional or yet-to-be developed manner including, for example, via a wired or wireless network, via a communications cloud, etc., and may comprise one or more microprocessors, and associated hardware, suitably programmed to receive and process signals from the fluidic fittings F1, F2, F3, etc.

It is also noted that recitations herein of "at least one" component, element, etc., should not be used to create an inference that the alternative use of the articles "a" or "an" should be limited to a single component, element, etc.

It is noted that recitations herein of a component of the present disclosure being "configured" or "programmed" in a particular way, to embody a particular property, or to function in a particular manner, are structural recitations, as opposed to recitations of intended use. More specifically, the references herein to the manner in which a component is "configured" or "programmed" denotes an existing physical condition of the component and, as such, is to be taken as a definite recitation of the structural characteristics of the component.

It is noted that terms like "preferably," "commonly," and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A threaded fluidic fitting comprising
a fluid passage,
at least one fluid port,
a threaded fitting portion,
an engageable body portion, and
an electro-fluidic leak detection element, wherein:
the fluid passage extends from the fluid port of the threaded fluidic fitting;
the threaded fitting portion comprises a helical thread, extends from a leak detection face of the engageable body portion, and is configured to rotate with the engageable body portion to enhance a fluidically sealed engagement of one of the fluid ports with a complementary fluidic component;
the electro-fluidic leak detection element is positioned on the leak detection face of the engageable body portion or on a drip edge portion of a face extending from the leak detection face of the engageable body portion; and the electro-fluidic leak detection element is configured as at least one of (i) a pair of concentric spaced electrodes surrounding a majority of a perimeter of the threaded fitting portion and (ii) a plurality of paired electrodes surrounding a majority of a perimeter of the threaded fitting portion where the threaded fitting portion extends from the leak detection face of the engageable body portion.

2. A threaded fluidic fitting as claimed in claim 1 wherein the electro-fluidic leak detection element is configured as a sensing portion surrounding a majority of a perimeter of the threaded fitting portion where the threaded fitting portion extends from the leak detection face of the engageable body portion.

3. A threaded fluidic fitting as claimed in claim 1 wherein the electro-fluidic leak detection element is configured as a plurality of spaced sensing portions surrounding a majority of a perimeter of the threaded fitting portion where the threaded fitting portion extends from the leak detection face of the engageable body portion.

4. A threaded fluidic fitting as claimed in claim 1 wherein the electro-fluidic leak detection element is positioned completely outside of the threaded fitting portion on the leak detection face of the engageable body portion.

5. A threaded fluidic fitting as claimed in claim 1 wherein:
the leak detection face of the engageable body portion is planar; and
the threaded fitting portion comprises a helical thread comprising an axis of rotation that intersects a plane of the leak detection face.

6. A threaded fluidic fitting as claimed in claim 1 wherein the electro-fluidic leak detection element comprises a printed circuit substrate and a fluid sensing portion secured to the printed circuit substrate.

7. A threaded fluidic fitting as claimed in claim 6 wherein the printed circuit substrate is mounted to the leak detection face of the engageable body portion.

8. A threaded fluidic fitting as claimed in claim 6 wherein:
the electro-fluidic leak detection element comprises printed circuitry electrically coupled to the fluid sensing portion of the electro-fluidic leak detection element; and
the fluid sensing portion and the printed circuitry are coated with a polymer selected to be resistant to degradation when in contact with fluid.

9. A threaded fluidic fitting as claimed in claim 1 wherein:
the leak detection element of the threaded fluidic fitting further comprises a leak detection module and printed circuitry electrically coupling the fluid sensing portion of the electro-fluidic leak detection element to the leak detection module; and
the leak detection module is secured to an outer surface of the threaded fluidic fitting.

10. A threaded fluidic fitting as claimed in claim 9 wherein the leak detection module is secured to the engageable body portion of the threaded fluidic fitting.

11. A threaded fluidic fitting as claimed in claim 1 wherein:
the threaded fluidic fitting further comprises a leak detection module communicatively coupled to the fluid sensing portions of the electro-fluidic leak detection element; and
the leak detection module is programmed to cooperate with the electro-fluidic leak detection element to generate a fluid leakage signal.

12. A threaded fluidic fitting as claimed in claim 11 wherein:
the electro-fluidic leak detection element comprises a plurality of fluid sensing portions; and
the leak detection module is programmed to cooperate with the fluid sensing portions to generate a fluid leakage signal indicative of a degree of leakage at the threaded fluidic fitting.

13. A threaded fluidic fitting as claimed in claim 2 wherein the sensing portion of the electro-fluidic leak detection element comprises at least one pair of electrodes.

14. A threaded fluidic fitting as claimed in claim 1 wherein the sensing portion of the electro-fluidic leak detection element comprises a conductive fluid sensor, a resistive fluid sensor, a capacitive fluid sensor, an optical fluid sensor, or combinations thereof.

15. A threaded fluidic fitting as claimed in claim 1 wherein:
the threaded fluidic fitting further comprises a barbed fitting portion and an additional electro-fluidic leak detection element;
the barbed fitting portion comprises a barb shank and a sealing barb;
the sealing barb and the barb shank are configured to form a sealed engagement with an inside diameter of an end portion of a length of fluidic tubing; and
the additional electro-fluidic leak detection element is positioned on the barb shank.

16. A threaded fluidic fitting as claimed in claim 15 wherein:
the electro-fluidic leak detection element comprises a printed circuit substrate and a fluid sensing portion secured to the printed circuit substrate; and
the printed circuit substrate is mounted to the barb shank.

17. A threaded fluidic fitting as claimed in claim 15 wherein the additional electro-fluidic leak detection element is configured as a plurality of spaced sensing portions arranged about an outer circumferential surface of the barb shank.

18. A barbed fluidic fitting comprising
a fluid passage,
at least one fluid port,
a barbed fitting portion, and
an electro-fluidic leak detection element, wherein:
the fluid passage extends from the fluid port of the barbed fluidic fitting;
the barbed fitting portion comprises a barb shank and a sealing barb;
the sealing barb and the barb shank are configured to form a sealed engagement with an inside diameter of an end portion of a length of fluidic tubing;
the electro-fluidic leak detection element is positioned on at least one of (i) the barb shank, wherein the electro-fluidic leak detection element is configured as a plurality of paired electrodes arranged about an outer circumferential surface of the barb shank and (ii) a leak detection face of an engageable body portion, where the electro-fluidic leak detection element is configured as at least one of (a) a pair of concentric spaced electrodes surrounding a majority of a perimeter of the barbed fitting portion and (b) a plurality of paired electrodes surrounding a majority of a perimeter of the barbed fitting portion.

19. A barbed fluidic fitting as claimed in claim 18 wherein:

the electro-fluidic leak detection element comprises a printed circuit substrate and a fluid sensing portion secured to the printed circuit substrate; and the printed circuit substrate is mounted to the barb shank.

20. A fluid handling system comprising a plurality of threaded fluidic fittings as claimed in claim 1 and a leak detecting computing hub in communication with the plurality of threaded fluidic fittings, wherein:

the leak detecting computing hub is configured to identify individual fittings of the plurality of fittings and process fluid leakage signals from each of the identified fittings; and the leak detecting computing hub is configured to build and store diagnostic data for each of the threaded fluidic fittings from the processed fluid leakage signals.

21. A fluid handling system comprising a plurality of barbed fluidic fittings as claimed in claim 18 and a leak detecting computing hub in communication with the plurality of barbed fluidic fittings, wherein:

the leak detecting computing hub is configured to identify individual fittings of the plurality of fittings and process fluid leakage signals from each of the identified fittings; and the leak detecting computing hub is configured to build and store diagnostic data for each of the barbed fluidic fittings from the processed fluid leakage signals.

22. A threaded fluidic fitting as claimed in claim 1, wherein:

the threaded fluidic fitting comprises at least two fluid ports; and the fluidic passage extends between the fluid ports of the threaded fluidic fitting.

* * * * *